(12) United States Patent
Holecko

(10) Patent No.: US 11,504,314 B2
(45) Date of Patent: Nov. 22, 2022

(54) MULTI-CHROME COSMETIC HAIR COMPOSITION

(71) Applicant: Hana Holecko, South San Francisco, CA (US)

(72) Inventor: Hana Holecko, South San Francisco, CA (US)

( * ) Notice: Subject to any disclaimer, the term of this patent is extended or adjusted under 35 U.S.C. 154(b) by 54 days.

(21) Appl. No.: 16/859,208

(22) Filed: Apr. 27, 2020

(65) Prior Publication Data

US 2021/0330563 A1    Oct. 28, 2021

(51) Int. Cl.

| | | |
|---|---|---|
| *A61K 8/31* | (2006.01) | |
| *A61K 8/81* | (2006.01) | |
| *A61K 8/41* | (2006.01) | |
| *A61K 8/37* | (2006.01) | |
| *A61K 8/891* | (2006.01) | |
| *A61K 8/34* | (2006.01) | |
| *A61K 8/26* | (2006.01) | |
| *A61K 8/25* | (2006.01) | |
| *A61Q 5/06* | (2006.01) | |
| *A61K 8/86* | (2006.01) | |

(52) U.S. Cl.
CPC .............. *A61K 8/315* (2013.01); *A61K 8/25* (2013.01); *A61K 8/26* (2013.01); *A61K 8/34* (2013.01); *A61K 8/37* (2013.01); *A61K 8/41* (2013.01); *A61K 8/817* (2013.01); *A61K 8/8152* (2013.01); *A61K 8/8158* (2013.01); *A61K 8/86* (2013.01); *A61K 8/891* (2013.01); *A61Q 5/065* (2013.01); *A61K 2800/412* (2013.01); *A61K 2800/436* (2013.01)

(58) Field of Classification Search
None
See application file for complete search history.

(56) References Cited

U.S. PATENT DOCUMENTS

| | | |
|---|---|---|
| 5,181,529 A | 1/1993 | Roberts |
| 5,468,477 A | 11/1995 | Kumar et al. |
| 6,190,648 B1 | 2/2001 | Kouzu et al. |
| 6,284,225 B1 * | 9/2001 | Bhatt .................... A61K 8/046 424/45 |
| 7,806,941 B2 | 10/2010 | Brun et al. |
| 7,981,404 B2 | 7/2011 | Dumousseaux |
| 10,383,797 B2 | 8/2019 | Simon et al. |
| 2007/0048239 A1 | 3/2007 | Song et al. |
| 2007/0107635 A1 | 5/2007 | Soane et al. |
| 2007/0141002 A1 | 6/2007 | Montezinos et al. |
| 2008/0299154 A1 | 12/2008 | Barrios et al. |
| 2010/0092409 A1 | 4/2010 | Amin et al. |
| 2010/0233114 A1 | 9/2010 | DeGeorge et al. |
| 2010/0260687 A1 | 10/2010 | Yu et al. |
| 2012/0031419 A1 | 2/2012 | Batt et al. |
| 2013/0133679 A1 | 5/2013 | Kergosien et al. |
| 2014/0202485 A1 | 7/2014 | Wang et al. |
| 2014/0348756 A1 * | 11/2014 | Doering .................. A61Q 11/00 424/43 |
| 2018/0243182 A1 | 8/2018 | Ricard et al. |
| 2018/0344589 A1 | 12/2018 | Litowitz |
| 2019/0192391 A1 | 6/2019 | Byren et al. |

OTHER PUBLICATIONS

Written Opinion of the International Searching Authority for PCT/US21/27029 established by the ISA/US completed on Jul. 7, 2021.

* cited by examiner

*Primary Examiner* — David J Blanchard
*Assistant Examiner* — Sarah J Chickos
(74) *Attorney, Agent, or Firm* — Goldstein Law Offices, P.C.

(57) ABSTRACT

A multi-chrome cosmetic hair composition is disclosed. The composition includes a base formula suitable for hair and an interference pigment providing a colored background exhibiting interference colors that are observable at different angles of observation. The formula is sufficient to enable a homogenous suspension of the interference pigment. The formula includes a propellant, denatured alcohol, neutralized octylacrylamide/acrylates/butylaminoethyl methacrylate copolymer 4, a neutralizing agent sufficient to neutralize the octylacrylamide/acrylates/butylaminoethyl methacrylate copolymer 4 to a range of 80% to 100%, and a plasticizer. The interference pigment includes an opaque-type interference pigment consisting of particles ranging from 5 microns to 60 microns in size to fill in gaps on hair shaft surfaces and create a smooth, chrome-like effect on the hair. The interference pigment includes an inorganic layer that specularly reflects incident light and semi-transparent inorganic layers that refract the reflected light such that the interference colors are observable.

16 Claims, 1 Drawing Sheet

MULTI-CHROME COSMETIC HAIR COMPOSITION

TECHNICAL FIELD

The present disclosure relates generally to cosmetic hair compositions. More particularly, the present disclosure relates to a cosmetic composition suitable for hair that exhibits a multichromatic color.

BACKGROUND

To emulate the appearance of multi-chrome hair, current cosmetic hair compositions and application systems are limited and unsatisfactory. One available option is to permanently alter the hair via bleaching and depositing dye to the hair.

However, this process is disadvantageous because it causes permanent damage to the hair, is very expensive, and requires hours of time investment, without ultimately achieving a truly multichromatic appearance. A second available option is to utilize temporary hair color spray. However, this process is also disadvantageous because these temporary hair color sprays offer a deposit of a single hue and are too sheer to achieve a true opaque color deposit on all hair types, particularly darker hair types. Further, temporary hair color sprays can stain the hair, which takes away from their effectiveness as temporary applications. Another available option is to utilize glitter hair sprays. However, glitter hair sprays are disadvantageous because glitter is reflective and unable to achieve a dramatic color shift as well as damaging to the environment because they often include microplastics.

Accordingly, there is a need for an easy-to-use multi-chrome cosmetic hair composition that is capable of providing a multi-chrome appearance to the hair, can be removed easily, and does not damage the hair or environment.

While these units may be suitable for the particular purpose employed, or for general use, they would not be as suitable for the purposes of the present disclosure as disclosed hereafter.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

BRIEF SUMMARY

An aspect of an example embodiment in the present disclosure is to provide a multi-chrome cosmetic composition suitable for the hair. Accordingly, the present disclosure provides a cosmetic composition including a high hold base formula that is capable of holding firmly on keratins and/or integuments and an interference pigment that provides a multichromatic effect to the hair when applied thereto.

An aspect of an example embodiment in the present disclosure is to provide a multi-chrome cosmetic composition that when applied to hair provides more than one observable color. Accordingly, the present disclosure provides a cosmetic composition including an interference pigment that when applied to hair provides a colored background whose color changes with the angle of observation.

An aspect of an example embodiment in the present disclosure is to provide a multi-chrome cosmetic composition for the hair that provides a high hold while preventing flaking of the composition when applied to the hair, thereby enabling the composition to provide a smooth and full coverage multi-chromatic appearance. Accordingly, the present disclosure provides a cosmetic composition including a base formula having a hair fixative for providing high hold and a plasticizer that reduces rigidity without reducing the hold provided by the hair fixative, thereby preventing flaking and increasing the smoothness of the cosmetic composition.

An aspect of an example embodiment in the present disclosure is to provide a multi-chrome cosmetic composition suitable for hair that is removable from hair with shampoo, or other hair cleaning agents. Accordingly, the present disclosure provides a multi-chrome cosmetic hair composition including a neutralizing agent configured to neutralize the pH of the hair fixative so as to enable removal of the composition with a hair cleaning agent.

An aspect of an example embodiment in the present disclosure is to provide a multi-chrome cosmetic composition suitable for the hair that is self-leveling, thereby enabling the composition to fill in the gaps on the hair shaft surfaces of the hair. Accordingly, the present disclosure provides a multi-chrome cosmetic hair composition including fine interference particles capable of filling in the gaps of the hair shaft surfaces to create a smooth, chrome-like effect, enhancing specularity and reducing sparkle effect.

The present disclosure addresses at least one of the foregoing disadvantages. However, it is contemplated that the present disclosure may prove useful in addressing other problems and deficiencies in a number of technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

BRIEF DESCRIPTION OF THE DRAWINGS

In the drawings, like elements are depicted by like reference numerals. The drawings are briefly described as follows.

FIG. 1 is a photograph of hair made up with a spray including the multi-chrome cosmetic hair composition according to one embodiment of the present disclosure.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete and fully conveys the scope of the present disclosure to those skilled in the art.

DETAILED DESCRIPTION OF THE PREFERRED EMBODIMENTS

FIG. 1 shows a photograph of hair made-up with the multi-chrome cosmetic hair composition of the present disclosure. The cosmetic composition comprises a physiological acceptable medium, or base formula, suitable for hair and one or more interference pigments. The base formula enables a homogeneous suspension of the one or more interference pigments when the one or more interference pigments are mixed therewith. The cosmetic composition, when applied to hair, provides a colored background whose color changes with the angle of observation. The cosmetic composition partly evaporates and dries quickly on contact with hair, enabling the interference pigment to fill in gaps, i.e., breaks, recesses, or raised edges on the surface of a hair shaft of the hair, and rest smoothly on the surface of the hair. The one or more inference pigments include very fine micron sized particles that are capable of filing in the majority, if not all, of the gaps on the hair shaft surface of the hair due to their small size. This creates a smooth, chrome-like effect and finish on the hair rather than a shimmery or sparkly finish, as can be seen in FIG. 1.

Base Formula

For the purposes of the present invention, the term "physiological acceptable medium" used interchangeable with "base formula" denotes a non-toxic medium that may be applied to human skin, lips, protein filaments, or integuments. The base formula denotes the cosmetic composition without the interference pigment.

The formulation of the base formula utilizes the same basic ingredients: a propellant or propellants, a solvent or solvents, an acrylic polymer or acrylic polymers, and a neutralizing agent or neutralizing agents.

The propellant used is Hydrofluorocarbon 152A. However, in other embodiments, the propellant used is Isobutane. In embodiments, the amount of Hydrofluorocarbon 152A ranges from 30% to 40% by weight, relative to the total weight of the cosmetic composition. In some embodiments, the amount of Hydrofluorocarbon 152A ranges from 34% to 39% by weight, relative to the total weight of the cosmetic composition. In one embodiment, the amount of Hydrofluorocarbon 152A is 37.847% by weight, relative to the total weight of the cosmetic composition.

The solvent or solvents used are ideally denatured alcohol (Alcohol Denat) (which may include t-Butyl Alcohol and/or Denatonium Benzoate), water, distilled water and/or Cyclopentasiloxane. In embodiments, the amount of denatured alcohol used in formulations of the base ranges from 45% to 65% by weight, relative to the total weight of the cosmetic composition. In some embodiments, the amount of denatured alcohol used in formulations of the base ranges from 50% and 60% by weight, relative to the total weight of the cosmetic composition. In one embodiment, the amount of denatured alcohol used in formulations of the base is 53.624% by weight, relative to the total weight of the cosmetic composition.

The acrylic polymer used is octylacrylamide/acrylates/butylaminoethyl methacrylate copolymer 4, also known as Amphomer®. In embodiments, the amount of octylacrylamide/acrylates/butylaminoethyl methacrylate copolymer 4 used in formulations of the base ranges from 2% to 7% by weight, relative to the total weight of the cosmetic composition. In some embodiments, the amount of octylacrylamide/acrylates/butylaminoethyl methacrylate copolymer 4 used in formulations of the base ranges from 3% and 6% by weight, relative to the total weight of the cosmetic composition. In other embodiments, the amount of octylacrylamide/acrylates/butylaminoethyl methacrylate copolymer 4 used in formulations of the base ranges from 4% and 5% by weight, relative to the total weight of the cosmetic composition. In one embodiment, the amount of octylacrylamide/acrylates/butylaminoethyl methacrylate copolymer 4 used in formulations of the base is 4.796% by weight, relative to the total weight of the cosmetic composition.

The acrylic polymer is carboxylated and must be completely or almost completely neutralized by a neutralizing agent for water solubility and shampoo removability. The ideal range of neutralization for octylacrylamide/acrylates/butylaminoethyl methacrylate copolymer 4 is 80% to 100% so as to yield a pH in the cosmetic composition ranging from 8.0 to 9.0. The level of neutralization may also alter the film properties, where higher neutralization provides a softer, more flexible feel, while lower neutralization imparts a harder, stiffer feel. Developing a higher hold creates for a smoother application and appearance of the interference pigment, achieving a true multi-chrome and/or metallic appearance. In embodiments, the octylacrylamide/acrylates/butylaminoethyl methacrylate copolymer 4 used in the formulation is neutralized to a range of 80% to 90%. In some embodiments, the octylacrylamide/acrylates/butylaminoethyl methacrylate copolymer 4 used in the formulation is 82% neutralized. In embodiments, the hold of the cosmetic composition as measured in joules is in the range of 0.008 to 0.1 joules as measured by a hair fiber tensile tester, such as the MTT175 or MTT690 from Dia-Stron Limited.

The neutralizing agent used to neutralize the acrylic polymer is Aminomethyl Propanol. However, in other embodiments, the neutralizing agent may be 2-amino-2-methyl-1,3-propanediol, dimethyl stearamine, mononisopropanolamine, and triisopropanolamine. The amount of neutralizing agent used in formulations of the base is Q.S. (quantum satis) and/or dependent upon how much acrylate copolymer is used in the formulations and the desired neutralization, e.g., pH, of the cosmetic composition.

To determine the amount of neutralizing agent required, the formula $B=W*A*N*E/1000$ is used. In this formula B denotes weight of base (neutralizing agent) needed (in grams), W denotes weight of acrylic polymer use, A denotes acidity in mEq/g (milliequivalents/gram) of the acrylic copolymer used, N denotes percentage (%) neutralization desired (in decimal form, i.e., 80% neutralization=0.80), and E denotes equivalent weight of base. For example, to neutralize 4.796% octylacrylamide/acrylates/butylaminoethyl methacrylate copolymer 4 by weight, relative to the total cosmetic composition to 82% neutralization, 1.109% Aminomethyl Propanol by weight, relative to the total weight of the cosmetic composition is required.

Optionally, plasticizers such as Triethyl Citrate and PEG/PPG-17/18 Dimethicone may be included in the base formulation. Plasticizers prevent the formulation from being too rigid without reducing the hold provided by the acrylic polymer. Further, plasticizers prevent the formula from flaking, improve the formulation's flexibility while supporting hold, softens the hair and adds body, as well as prevent stickiness of the formulation. Specifically, the Triethyl Citrate helps with film-forming, i.e., humidity resistance and prevents flaking, and the PEG/PPG-17/18 Dimethicone helps with flexibility, body, conditioning, and acts as a surfactant, i.e., helps with the washing-off of the cosmetic composition from hair. If a plasticizer or plasticizer is included in the cosmetic composition, more neutralizing agent, in addition to the neutralizing agent used to neutralize the acrylic polymer, may be required to neutralize the plasticizer and bring the overall pH of the cosmetic composition within acceptable limits, e.g., 8.0-9.0.

In embodiments, a range of 0.03% to 1% of Triethyl Citrate by weight, relative to the total weight of the composition is used in the formulation. In some embodiments, the amount of Triethyl Citrate used in the formulation is 0.04% to 0.08% by weight, relative to the total weight of the composition. In one embodiment, the amount of Triethyl Citrate used in the formulation is 0.06% by weight, relative to the total weight of the composition. In embodiments, a range of 0.03% to 1% of PEG/PPG-17/18 Dimethicone by weight, relative to the total weight of the composition is used in the formulation. In some embodiments, the amount of PEG/PPG-17/18 Dimethicone used in the formulation is 0.04% to 0.08% by weight, relative to the total weight of the composition. In one embodiment, the amount of PEG/PPG-17/18 Dimethicone used in the formulation is 0.06% by weight, relative to the total weight of the composition. In embodiments, Triethyl Citrate and PEG/PPG-17/18 Dimethicone are both used in formulation in accordance with the above ranges. Preferably, the Triethyl Citrate and PEG/PPG-17/18 Dimethicone are used in equal amounts when both used in the formulation. For example, if 0.06% w/w of Triethyl Citrate is used in the formulation then 0.06% w/w of PEG/PPG-17/18 Dimethicone should be used in the formulation.

Optionally, additional chemicals and/or compounds designed to appeal to consumers ("Marketing Compounds"), which further enhance the cosmetic composition, may be included, such as conditioners and emollients, including, but not limited to, Panthenol, Hydrolyzed Soy Protein, Pentaerythrityl Tetracaprylate/Tetracaprate, and *Helianthus annuus* (Sunflower) Seed Oil. For example, in embodiments, a range of 0% to 1% of Panthenol by weight, relative to the total weight of the composition is used in the formulation. In one embodiment, 0.060% of Panthenol by weight, relative to the total weight of the composition is used in the formulation. In some embodiments, a range of 0% to 1% of Hydrolyzed Soy Protein by weight, relative to the total weight of the composition is used in the formulation. In one embodiment, a range of 0.060% of Hydrolyzed Soy Protein by weight, relative to the total weight of the composition is used in the formulation. In other embodiments, a range of 0% to 1% of Pentaerythrityl Tetracaprylate/Tetracaprate by weight, relative to the total weight of the composition is used in the formulation. In one embodiment, 0.060% of Pentaerythrityl Tetracaprylate/Tetracaprate by weight, relative to the total weight of the composition is used in the formulation. In certain embodiments, a range of 0% to 1% of *Helianthus annuus* (Sunflower) Seed Oil by weight, relative to the total weight of the composition is used in the formulation. In one embodiment, 0.028% of *Helianthus annuus* (Sunflower) Seed Oil by weight, relative to the total weight of the composition is used in the formulation.

Interference Pigment

For the purposes of the present invention, the term "interference pigment" denotes an agent for obtaining, when the cosmetic composition is applied to hair, a color trajectory in the a*b* plane of the CIE L*a*b* 1976 colorimetric space corresponding to a variation Dh of the hue angle h of at least 20° when the angle of observation relative to the normal is varied between 0° and 80°, for an incident light angle of 45°.

Further, for the purposes of the present invention, an interference pigment makes it possible to observe a color change, also known as a "color flop" or "color shift" as a function of the angle of observation, which is greater than the change that may be encountered with nacres. Moreover, an interference pigment makes it possible to view interference colors, or those colors that are a product of constructive and/or destructive wave interference, thereby leading to more brilliant, and high-chroma (high color saturation) hues. The color shift and high-chroma is further enhanced by the use of opaque-type interference pigments, discussed below. The presence of high-chroma hues and dramatic color shift can be noted from FIG. 1.

In embodiments, the interference pigment comprises an opaque-type interference pigment, or those including an opaque inorganic core, such as aluminum, as opposed to transparent- or semi-transparent-type interference pigments that include a transparent or semi-transparent core such as mica. An aspect of the present disclosure is to obtain high-chroma hues or colors, which is influenced by highly reflective and non-transparent surfaces such as aluminum.

In embodiments, the amount of interferences pigment used in the cosmetic composition ranges from 1% to 4% by weight, relative to the total weight of the cosmetic composition. In some embodiments, the amount of interferences pigment used in the cosmetic composition ranges from 2% to 3% by weight, relative to the total weight of the cosmetic composition. In one embodiment, the amount of interferences pigment used in the cosmetic composition is 2.298% by weight, relative to the total weight of the cosmetic composition.

The interference pigment may be chosen so as to present a relatively large color change with the angle of observation. The interference pigment may thus be chosen such that a color difference $\Delta E$ of the cosmetic composition, measured in the CIE L*a*b* 1976 colorimetric space, of at least 2 may be observed for a variation of the angle of observation of between 0° and 80° under illumination at 45°.

The interference pigment may also be chosen such that a variation Dh of the hue angle of the cosmetic composition, in the CIE L*a*b* 1976 plane, of at least 30° or even at least 40° or at least 60°, or even at least 100°, may be observed for an illumination at 45° and a variation of the angle of observation of between 0° and 80°.

The interference pigment comprises a plurality of multilayer interference particles, such as flakes or other plate-like particles that include stacked layers. In embodiments, each of the multilayer interference particles ranges from 5 microns to 60 microns or 5 microns to 25 microns in size and includes an opaque/non-transparent, inorganic core layer surround by stacked semi-transparent or transparent inorganic layer or layers. Given the opacity of the opaque/non-transparent inorganic core layer, the core layer is configured to specularly reflect incident light, while the surrounding inorganic layer(s) are configured to reflect incident light as well as refract the light reflected from the opaque core layer via interference, so as to reflect a plurality of interference colors having high-chroma. In some embodiments, the surrounding inorganic layers are configured to absorb specific wavelengths of light so as to reflect or refract other specific wavelengths of light and make only certain colors observable on the surface of the interference particles.

The layers, which may or may not be independent of each other, may comprise at least one material chosen from the group consisting of the following materials: $MgF_2$, $CeF_3$, ZnS, ZnSe, Si, $SiO_2$, Ge, Te, $Fe_2O_3$, Pt, Va, $Al_2O_3$, MgO, $Y_2O_3$, $S_2O_3$, SiO, $HfO_2$, $ZrO_2$, $CeO_2$, $Nb_2O_5$, $Ta_2O_5$, $TiO_2$, Ag, Al, Au, Cu, Rb, Ti, Ta, W, Zn, $MoS_2$, cryolite, and alloys, polymers and combinations thereof. The multilayer interference structure may or may not have, relative to the central core layer, symmetry in the chemical nature of the stacked layers.

In embodiments, the interference pigment includes a three-layer structure comprising an opaque inorganic core layer, a glass-like inorganic layer, and a semi-transparent metal oxide layer. In some embodiments, the opaque inorganic core comprises aluminum, the glass-like transparent inorganic layer comprises silica ($SiO_2$) and metal oxide may comprise iron oxide, titanium dioxide, aluminium oxide, magnesium oxide, zinc oxide, or chromium oxide, or combinations thereof. In some embodiments, the chemical composition of the interference pigment includes aluminum in an amount ranging from 2% to 26% by weight, relative to the total weight of the interference pigment, silica in an amount ranging from 47% to 96% by weight, relative to the total weight of the interference pigment, and iron oxide in an amount ranging from 1% to 27% by weight, relative to the total weight of the interference pigment. In embodiments, the iron oxide is selected from the group consisting of $FeO$, $FeO_2$, $Fe_3O_4$, $Fe4O5$, $Fe5O6$, $Fe_5O_7$, $Fe_{25}O_{32}$, $Fe_{13}O_{19}$, $Fe_2O_3$, $Fe(OH)_2$, and $Fe(OH)_3$.

In embodiments, the interference pigment used for the cosmetic composition comprises one or more of the interference pigments sold under the name CHROMASHIFT by KOLORTEK and having the following product codes KT-BO1060, KT-BR1060, KT-GO1060, KT-GPB525, KT-GRB525, KT-OG1060, KT-PYB525, KT-RG1060, KT-RYB525, and KT-YS1060. In some embodiments, the interference pigment used for the cosmetic composition comprises one or more of the interference pigments sold under the name CHROMAFLAIR by VIAVI and having the following product codes RED/GOLD 000, SILVER/GREEN 060, GOLD/SILVER 080, GREEN/PURPLE 190, CYAN/PURPLE 230, BLUE/RED 280, and MAGENTA/GOLD 334. In other embodiments, the interference pigment used for the cosmetic composition comprises one or more of the interference pigments sold under the name DUOCROME, REFLECKS MULTIDIMENSIONS, and REFLECKS MULTIREFLECTIONS by BASF and having the following product codes YR422C, YG 822C, RY 224C, RO 324C, RV 524C, RB 624C, BY 226C, BR 426C BV 526C, BG826C, GY 227C, GLISTENING GOLD G280D, CHANGING CHERRY G480D, VARYING VIOLET G580D, SHIFTING SAPPHIRE G680D, TRANSFORMING TEAL G780D, TWISTED TERRACOTTA G390D, and SWIRLING SWEETBERRY G490D. In certain embodiments, the interference pigment used for the cosmetic composition comprises one or more of the interference pigments sold under the name DIAMOND VARIABLE, GLASSMIRA, SILIKMIRA, and MICAMIRA by SANDREAM and having the following product codes DIAMOND VARIABLE GV 27, GLASSMIRA GG88, SILIKMIRA SLEEK BVR SVS-669, and MICAMIRA BRO28. In further embodiments, the interference pigment used for the cosmetic composition comprises one or more of the interference pigments sold under the name K-RAY PERPETUAL and KOBOPEARL PERPETUAL by KOBO and having the following product codes KOBOPEARL PERPETUAL 10 PASTELGOLD and KOBOPEARL PERPETUAL SHEEN VIOLETRED.

In some formulations, multiple interference pigments may be required in order to obtain the desired multi-chromatic appearance, or range of specific colors based on viewing angles.

According to one aspect of the present disclosure, the cosmetic composition features the use of at least one interference pigment capable of creating interference colors that are visible to the naked eye at different viewing angles, in a hair cosmetic composition intended to provide a multichromatic effect, in which all observable colors include high-chroma.

In one implementation example, the interference pigment is applied in the form of a composition as defined above.

EXAMPLES

The following examples are for illustrative purposes only and are not intended to limit the scope of the claims. The examples are prepared by mixing the chemicals/compounds using techniques standard in the hair cosmetics industry. The percentages below are all expressed in a weight basis relative to the total weight of the cosmetic composition. The invention applies most particularly to compositions intended to be applied to hair.

Example 1

The following example shows the allowable range of percentages by weight of each of the chemicals/compounds that form the cosmetic composition.

| INGREDIENT NAME | % BY WEIGHT OF THE COMPOSITION (WORKABLE RANGES) |
| --- | --- |
| ALCOHOL DENAT | 45-65 |
| HYDROFLUOROCARBON 152A | 30-40 |
| OCTYLACRYLAMIDE/ACRYLATES/ BUTYLAMINOETHYL METHACRYLATE COPOLYMER 4 | 2-7 |
| AMINOMETHYL PROPANOL | Q.S.* |
| INTERFERENCE PIGMENT (CHROMASHIFT SOLD BY KOLORTEK: PRODUCT CODE KT-GRB525) | 1-4 |
| TRIETHYL CITRATE | 0.03-1 |
| PEG/PPG-17/18 DIMETHICONE | 0.03-1 |
| PANTHENOL | 0-1 |
| HYDROLYZED SOY PROTEIN | 0-1 |
| PENTAERYTHRITYL TETRACAPRYLATE/ TETRACAPRATE | 0-1 |
| *HELIANTHUS ANNUUS* (SUNFLOWER) SEED OIL | 0-1 |

*Quantum satis

Example 2

The following example shows an ideal percentage by weight of each of the chemicals/compounds that form the cosmetic composition. FIG. 2 displays a photograph of hair made-up with the following example.

| INGREDIENT NAME | % BY WEIGHT OF THE COMPOSITION |
| --- | --- |
| ALCOHOL DENAT | 53.624 |
| HYDROFLUOROCARBON 152A | 37.847 |
| OCTYLACRYLAMIDE/ACRYLATES/ BUTYLAMINOETHYL METHACRYLATE COPOLYMER 4 | 4.796 |
| AMINOMETHYL PROPANOL | 1.109 |
| INTERFERENCE PIGMENT (CHROMASHIFT SOLD BY KOLORTEK: PRODUCT CODE KT-GRB525) | 2.298 |
| TRIETHYL CITRATE | 0.060 |
| PEG/PPG-17/18 DIMETHICONE | 0.060 |
| PANTHENOL | 0.060 |

| INGREDIENT NAME | % BY WEIGHT OF THE COMPOSITION |
| --- | --- |
| HYDROLYZED SOY PROTEIN | 0.060 |
| PENTAERYTHRITYL TETRACAPRYLATE/ TETRACAPRATE | 0.060 |
| *HELIANTHUS ANNUUS* (SUNFLOWER) SEED OIL | 0.028 |

It is understood that when an element is referred hereinabove as being "on" another element, it can be directly on the other element or intervening elements may be present therebetween. In contrast, when an element is referred to as being "directly on" another element, there are no intervening elements present.

Moreover, any components or materials can be formed from a same, structurally continuous piece or separately fabricated and connected.

It is further understood that, although ordinal terms, such as, "first," "second," "third," are used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Example embodiments are described herein with reference to cross section illustrations that are schematic illustrations of idealized embodiments. As such, variations from the shapes of the illustrations as a result, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

In conclusion, herein is presented a multi-chrome cosmetic hair composition. The disclosure is illustrated by example in the drawing figures, and throughout the written description. It should be understood that numerous variations are possible, while adhering to the inventive concept. Such variations are contemplated as being a part of the present disclosure.

What is claimed is:

1. A multi-chrome cosmetic hair composition, comprising:
a propellant in an amount ranging from 30% to 40% by weight, relative to the total weight of the composition;
neutralized octylacrylamide/acrylates/butylaminoethyl methacrylate copolymer 4 in an amount ranging from 2% to 7% by weight, relative to the total weight of the multi-chrome cosmetic composition, the octylacrylamide/acrylates/butylaminoethyl methacrylate copolymer 4 neutralized to a range of 80% to 100%;
an interference pigment in an amount ranging from 1% to 4% by weight, relative to the total weight of the composition, the interference pigment comprising a plurality of particles, each of the plurality of particles including an aluminum opaque inorganic core surrounded by a metal oxide semi-transparent inorganic layer;
denatured alcohol in an amount ranging from 45% to 65% by weight, relative to the total weight of the composition; and
a neutralizing agent in an amount sufficient to neutralize the octylacrylamide/acrylates/butylaminoethyl methacrylate copolymer 4 to a range of 80% to 100%;
wherein:
the neutralizing agent is in an amount sufficient to generate a pH in the composition ranging from 8.0 to 9.0; and
the propellant is hydrofluorocarbon 152A.

2. The composition of claim 1, wherein the neutralizing agent is selected from the group consisting of aminomethyl propanol, 2-amino-2-methyl-1,3-propanediol, dimethyl stearamine, mononisopropanolamine, and triisopropanolamine.

3. The composition of claim 2, wherein the neutralizing agent is aminomethyl propanol.

4. The composition of claim 3, further comprising:
a first plasticizer in an amount 0.03% to 1% by weight, relative to the total weight of the composition.

5. The compositions of claim 4, further comprising:
a second plasticizer in an amount 0.03% to 1% by weight, relative to the total weight of the composition.

6. The composition of claim 5, wherein the amount of first plasticizer by weight, relative to the total weight of the compositions is equal to the amount of second plasticizer by weight, relative to the total weight of the composition.

7. The composition of claim 6, wherein:
the first plasticizer is triethyl citrate; and
the second plasticizer is PEG/PPG-17/18 Dimethicone.

8. The composition of claim 7, wherein the interference pigment includes a surface configured to reflect a plurality of interference colors, each of the plurality of interference colors observable at a different angle of observation relative to the surface of the pigment.

9. The composition of claim 8, wherein:
each of the plurality of particles ranges from 5 microns to 60 microns in size
the aluminum opaque inorganic core is configured to specularly reflect incident light; and
the metal oxide semi-transparent inorganic layer is configured to refract the plurality of interference colors.

10. The composition of claim 9, wherein the metal oxide is selected from the group consisting of iron oxide, titanium dioxide, aluminum oxide, magnesium oxide, zinc oxide, and chromium oxide.

11. The composition of claim 10, wherein the interference pigment further comprises a glass-like layer surrounding the opaque inorganic core, the glass-like layer disposed between the opaque inorganic core and the semi-transparent inorganic layer.

12. The composition of claim 11, wherein the glass-like layer is silica.

13. The composition of claim 12, wherein the interference pigment comprises aluminum in an amount ranging from 2% to 26% by weight, relative to the total weight of the interference pigment.

14. The composition of claim 13, wherein the interference pigment further comprises iron oxide in an amount ranging from 1% to 27% by weight, relative to the total weight of the interference pigment.

15. The composition of claim 14, wherein the interference pigment further comprises silica in an amount ranging from 47% to 96% by weight, relative to the total weight of the interference pigment.

16. The composition of claim 15, wherein the iron oxide is selected from the group consisting of $FeO$, $FeO_2$, $Fe_3O_4$, $Fe_4O_5$, $Fe_5O_6$, $Fe_5O_7$, $Fe_{25}O_{32}$, $Fe_{13}O_{19}$, $Fe_2O_3$, $Fe(OH)_2$, and $Fe(OH)_3$.

* * * * *